United States Patent [19]
Hölter et al.

[11] Patent Number: 4,992,965
[45] Date of Patent: Feb. 12, 1991

[54] CIRCUIT ARRANGEMENT FOR THE EVALUATION OF A SIGNAL PRODUCED BY A SEMICONDUCTOR GAS SENSOR

[75] Inventors: Heinz Hölter, Gladbeck; Hanns Rump, Unna-Massen, both of Fed. Rep. of Germany; Helmut Vietze, Frauenfeld, Switzerland

[73] Assignee: Eftag-Entstaubungs- und Fordertechnik AG, Biel, Switzerland

[21] Appl. No.: 294,606

[22] Filed: Nov. 30, 1988

[30] Foreign Application Priority Data

Apr. 2, 1987 [CH] Switzerland ............ 1308/87
Apr. 2, 1987 [CH] Switzerland ............ 1306/87
Mar. 31, 1988 [WO] PCT Int'l Appl. . PCT/EP88/00269

[51] Int. Cl.$^5$ .............. G08B 17/10; F25B 29/00; G06F 7/00
[52] U.S. Cl. .................. 364/551.01; 364/424.05; 340/634; 73/31.06; 165/16; 98/2.11; 236/49.3
[58] Field of Search ......... 364/551.01, 424.05, 364/148, 497; 236/49.3; 73/23, 27; 98/2.01, 2.11; 340/628, 632, 634; 165/16, 42

[56] References Cited

U.S. PATENT DOCUMENTS

| | | | |
|---|---|---|---|
| 3,418,914 | 12/1968 | Finkin | 340/632 X |
| 4,259,722 | 3/1981 | Iwata et al. | 165/42 X |
| 4,390,869 | 6/1983 | Christen et al. | 340/634 X |
| 4,437,391 | 3/1984 | Eguchi et al. | 98/2.01 |
| 4,458,583 | 7/1984 | Fukui et al. | 236/49.3 X |
| 4,478,049 | 10/1984 | Fukui et al. | 165/16 X |
| 4,586,143 | 4/1986 | Kaneyasu | 340/634 X |
| 4,665,385 | 5/1987 | Henerson | 73/23 X |
| 4,785,658 | 11/1988 | Jackson | 73/23 |
| 4,847,783 | 7/1989 | Grace et al. | 364/497 |
| 4,875,406 | 10/1989 | Hölter et al. | 98/2.01 |
| 4,896,143 | 1/1990 | Dolnick et al. | 340/634 |
| 4,916,913 | 4/1990 | Narikiyo | 236/49.3 X |

*Primary Examiner*—Joseph L. Dixon
*Attorney, Agent, or Firm*—Herbert Dubno; Yuri Kateshov

[57] ABSTRACT

A circuit for the evaluation of a signal produced by a semiconductor gas sensor provides a reliable control for manipulating a recirculated air valve in motor vehicles and their air-conditioning systems and includes a voltage divider connected with an integrator having a time constant bigger than time needed for reaching a peak of noxious gases outside of the motor vehicle.

8 Claims, 3 Drawing Sheets

CIRCUIT ARRANGEMENT FOR THE EVALUATION OF A SIGNAL PRODUCED BY A SEMICONDUCTOR GAS SENSOR

FIELD OF THE INVENTION

The invention relates to a circuit arrangement for the evaluation of a signal produced by a semiconductor gas sensor, for the purpose of controlling the recirculated-air valves in motor vehicles and in their air-conditioning systems.

Background of the Invention

It is desirable to act upon the ventilation system of a motor vehicle in such a manner that, when noxious substances are present in the outside air, a valve closes the ventilation system, so that no more air can come from outside and the inner air-recirculation system starts to operating. p Methods are known which are based on the detection of the state of the outside air with the aid of a semiconductor sensor. As a rule, the sensor element is connected in series with an ohmic resistor, so that a voltage divider results.

It is disadvantageous that a semiconductor sensor, besides being sensitive to noxious substances, has a cross-sensitivity towards temperature and air humidity. As a result, when the control switch is set, the switching point in time is very strongly dependent on external conditions. Therefore, such circuits are not usable.

Further, it has been proposed to read only the alternating component of voltage—e.i. the change—at the voltage divider and to process it further, which has as a result that the slow gradients—such as temperature and humidity—do not reach the evaluation. In practice, this method has also proven to be disadvantageous.

Furthermore, it has been proposed to send the sensor signal at the voltage divider over a timer with a very high time constant. According to results, at the outlet end of this timer stands an integral of the sensor voltage.

In the simplest case, this timer can consist of a resistor/capacitor combination. But in view of the high integration times, it is recommendable to use digital integrator circuits. However, the selection of the circuit is of minimal importance for the method described hereafter.

It is further known to feed the output signals of a sensor detecting noxious substances to a circuit element, whereby when a certain output threshold is reached, the arrangement gives off a switch impulse which closes the air-recirculation valve. In this known method, the changes of the sensor signal under the influence of air humidity and air temperature are not taken into consideration. This fact leads to switch-point changes. Additionally, the local load of noxious substances is not considered. This means that, for instance, in industrial areas of large cities the load of noxious substances in the air is higher than in rural areas.

Starting from this state of the art, the invention has the obJect to improve a circuit arrangement of the afore-described type in such a way that its switching behavior is more reproducible and corresponds adequately to the physiological needs of humans taking into consideration the local load, i.e. the background level, including it in the system.

In order to solve this problem, the invention proposes to use a voltage divider connected with an integrator for regulating the sensitivity of a sensor detecting a level of noxious gases outside of a motor vehicle.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
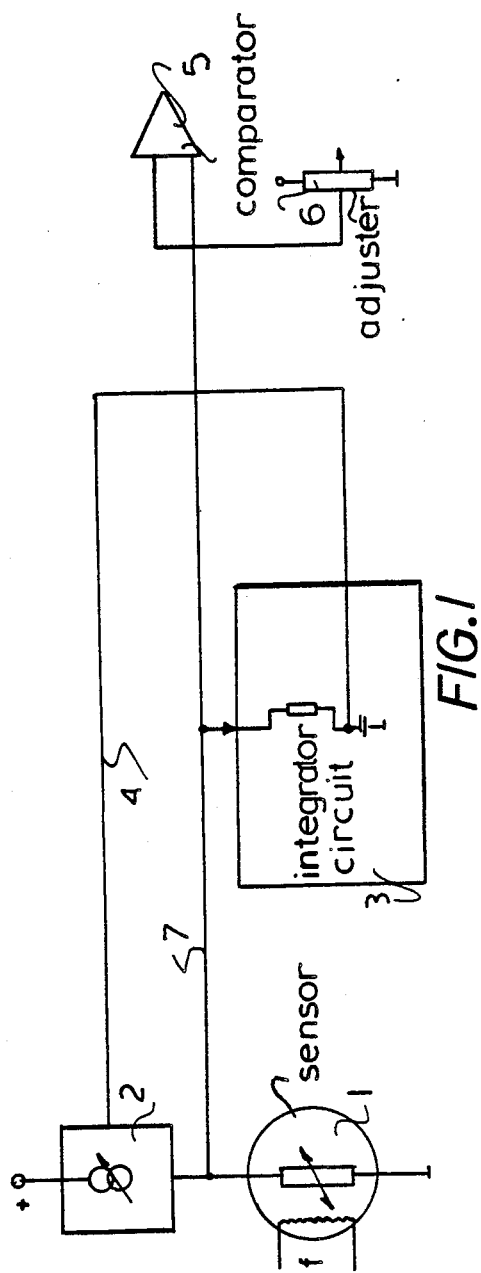
FIG. 1 is a block diagram of a first embodiment.
Figure 2:
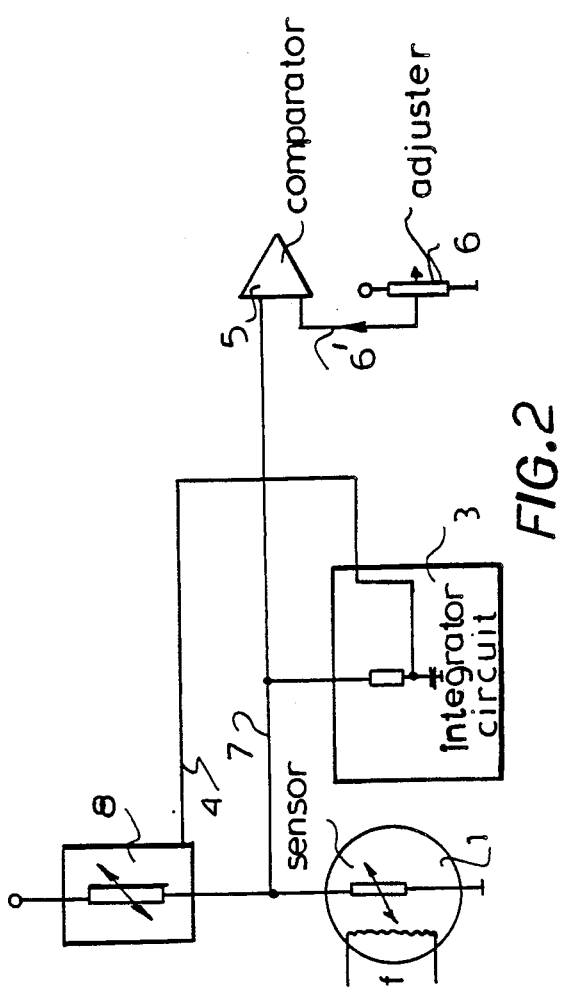
FIG. 2 is a block diagram of a second embodiment.

In the embodiments according to FIGS. 1 and 2, the sensor 1 is connected in series with a constant-current source 2. The resulting sensor signal 7 is first fed to the input end of a comparator 5 and secondly is directed over a an integrator circuit 3, so that at the output end of this integrator circuit an integrated sensor signal 4 appears.

At a constant sensor voltage, after a while, this integration voltage 4 is going to be identical. The integration voltage is fed into the constant-current source 2 as a disturbance-variable feed-forward element, whereby the active direction is such that the constant current increases, whenever the integration voltage is lower than a preestablished value.

According to results, it is achieved that the system tends to keep the sensor voltage 7 at a certain level.

According to experience, the variations in the road traffic and translated into impulse-like peaks of noxious substances, primarily in situations such as jams at traffic lights, in tunnels, underground garages, etc. In opposition. thereto, long-term influences (local loads, temperature, humidity) change extremely slowly.

When the integration time of the integrator 3 is clearly bigger than the time in which normally peaks of noxious substances occur, then the comparator 5 reliably detects these noxious-substances peaks and switches, whereby the switch point can be selected through an adjuster 6 producing a predetermined signal 6', which can also be a fixed resi In a further embodiment of the invention FIG. 2 the constant-current source is replaced by an adjustable resistor 8, e.g. a FET-transistor which is provided in the control loop. The active mechanism is comparable. The system tries to keep the voltage in the voltage divider constant, whereby the time delay acts.

The invention solves advantageously the problem of controlling the operation point of the comparator 5 independently from the influence of values in such a manner as to trigger a switch signal whenever a variation in the noxious substances occurs, whose rise is quicker then the integration time of the integrator 3.

Figure 3:
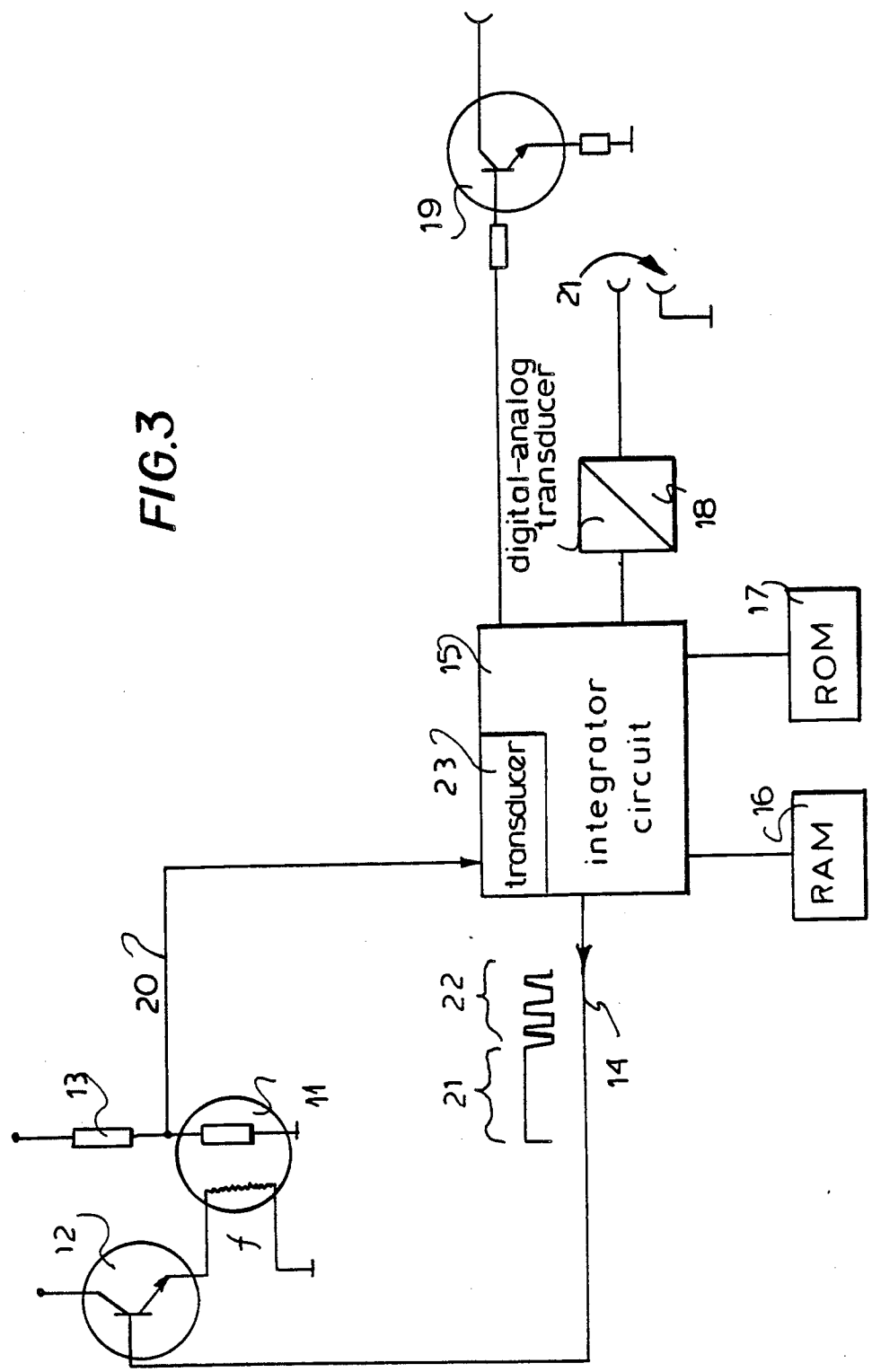
FIG. 3 is a block diagram of a third embodiment.
Figure 4:
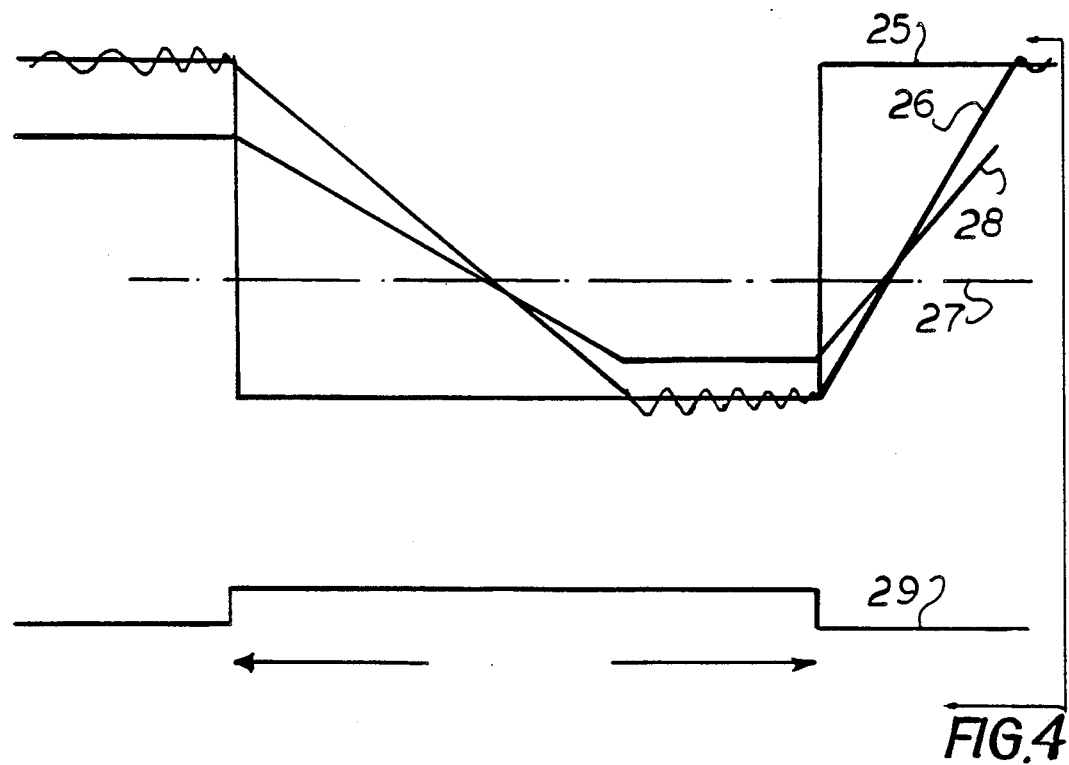
FIG. 4 is a diagram showing the modus operandi of the block diagram according to FIG. 3.

In the embodiment of FIG. 3 and FIG. 4, the sensor 11 forms a voltage divider with the resistor 13. A sensor voltage 20 is created. The resistor 13 can be replaced with the same results by a constant-current source. The sensor voltage is digitized by a digital-analog transducer, which preferably is a component of a microprocessor 15. The program of the microprocessor 15 is solidly stored in a ROM 17. The microprocessor 15 gives a switch signal for a transistor with open-collector output 19. Alternately or simultaneously, an analog signal 21 can be emitted, which is created by the processor in a digital-analog transducer 18. The circuit is to be used preferably in the motor vehicle wherein the board voltage is usually 12 volt. The majority of semiconductor sensors have to be heated, whereby the filament power has to be very carefully observed and it normally amounts to 5 volt.

When the constant filament power is to be produced with the aid of a stabilizer, the loss of heat is quite considerable. Therefore, it is proposed to obtain the filament power so that, with the aid of a switching transistor 12, a higher voltage than the heating voltage is pulsed in a proportion which produces effectively the same filament power as when the sensor 11 is heated with 5-volt direct current. In the preferred embodiment, the 12-volt board voltage is stabilized to 8 volt, with the help of a stabilizer.

The program switches the switching transistor 12, which becomes conductive after being switched on, so that over a period of time which can be preselected at will—in the preferred embodiment 30–60 sec—the sensor 11 is heated with an almost double filament power than the one normally used. The advantage of this preheating is that the sensor 11 "cleanses" itself very quickly, thus becoming operational. After this time span, the program produces an impulse, whose spacing ratio is so measured that the effective filament power corresponds to the data sheet of the sensor.

The program then waits for a further, also freely selectable time span, until the sensor 11 resumes its normal operation data. After that, the program compares whether the sensor voltage detected by the A/D-transducer 23 signals the presence of a noxious-substance level. If this is present, the switch output end 19 is activated. At the same time, the program forms an average value (integral) of the sensor voltage. In a relatively slow time loop, the given switching level is adjusted. In the preferred embodiment, the adjustment speed is independent from the height of the respective sensor voltage. The program only checks whether the sensor voltage is higher than the internally created comparison level. If the comparison level does not correspond to the sensor voltage, the register correspondingly deducts, respectively adds 1 bit. Expressed in a simple manner, the comparison level follows the sensor level, but very much delayed in time. Since, as experience teaches, noxious-substance peaks occur temporarily with very high gradients, these will certainly lead to a triggering of the switching contact, in the arrangement according to the invention. On the contrary, slow, creeping loads of noxious substances, such as typically occurring due to humidity, temperature and local loads, are "learnt" and adjust the switching level.

The program can be set up in such a way that in the case of peaks of noxious substances increasing quicker than a preselected gradient, the detection speed is slowed down. Thereby it is achieved that the sensitivity of the circuit arrangement is not unduly modified due to frequently occurring noxious-substance peaks.

If a certain noxious-substance level is surpassed and becomes a matter of an objective health hazard, the "learning" is interrupted. Furthermore, when this level is surpassed, the valve will remain permanently closed.

Most sensors for noxious substances have a variable mu characteristic. It follows that in the case of a very low local load (clean air), the influence of already very small amounts of noxious substances will lead to a relatively high voltage variation. When the local load is higher, i.e. in the case of already loaded air, the characteristic curve of the sensor becomes flatter, leading to the fact that equal variations in the amount of noxious substances result in clearly lower voltage variations.

In accordance with the invention, this fact is taken into account by that the switching threshold does not follow the sensor signal parallely. The distance between the sensor signal and the switching threshold is rather diminished with the increasing load of noxious substances, whereby the interrelation can be linear or non-linear.

As a result of this measure, it is achieved that, in the case of increasing local load, the sensitivity towards impulse-like loads of noxious substances remains the same, besides, when the air is not loaded, the sensitivity of the arrangement is considerably enhanced. However, since the switching interval is somewhat bigger, it is insured that the valve closes only then, when an objectively and subjectively disturbing level of noxious substances is reached.

In a further embodiment of the invention, the "learning speed" in the first minute after start is particularly high, so that the device can detect especially early possible extreme deviations from the preestablished value.

Further, it is proposed in accordance with the invention to clearly reduce once more the detection speed in a separate program section. The difference between this extremely integrated signal and the sensor voltage is meant to serve for the indication of the sensor level. Therefore, this signal is emitted over a D/A transducer 18 and can be displayed by any desired means.

Since it is conceivable that the internally formed "learnt" signal can be temporarily higher than the sensor level (Example: when travelling through a very long tunnel with high local load), it is insured that "negative levels" can never be created. Therefore the program is developed in such a manner that the internal comparison value of each improvement of the air situation signaled by the sensor voltage, follows very rapidly or even immediately.

The modification of the internal switching level (reference level) is not kept constant in the described embodiment of the invention, but in correspondence with the present average sensor level. This problem is solved by creating an average sensor level, as an auxiliary reference level. The actual switching level is created according to an algorithm, calculated from the mean value between the just mentioned reference level and the level leading to the permanent shutting of the valve.

In RAM 16 the operandi are kept in intermediate storage, i.e. the values which result from the integration as computed data.

From the diagram in FIG. 4, the modus operandi of the circuit arrangement according to the invention can be seen.

The curve 25 is a theoretical sensor voltage, which has a rectangular character. The curve 26 represents the internal reference level, which, in the beginning, is identical to the level 25 and follows it in a linear function, then later in time catches up with it, and, after the level 25 has increased again, trails it once again, in order to catch up with it later.

The line 27 represents the level at which the valve should always be closed. The actual switching level is calculated from any pondered value from the curve 25 and 26 and is represented in the drawing as curve 28. The curve 29 shows when the valve is closed, as a result of the above.

The position of the curve 27 can be selected at will. The relationship between the curves 27 and 26 can have any desired proportionality.

The closed-time of the valve is canceled after a freely adjustable time, so that there is no health hazard to the occupants of the vehicle due to lack of oxygen. Besides, this time span depends on the size of the cabin. This termination of the closed-time is also advantageous for activation, in order to bring in an impulse of fresh air to flush the cabin. The constant switching level "heat on" after the start of the program is marked with 21 and the pulsed heating with 22. The pulse output of the microprocessor 15 to the heating system is marked with 14.

We claim:

1. A gas-sensing system for controlling an air-recirculation valve in a motor vehicle having an interior to which air from outside can be supplied or in which air can be recirculated in accordance with a setting of the air-recirculation valve, said sensing system comprising:
   a semiconductor sensor providing an output signal corresponding to a concentration of external noxious gases having a critical high level of the concentration;
   an adjustable electricity source connected in series with said sensor and forming therewith a voltage divider;
   control means connected with said divider and receiving the output signal for realizing a time delay of said output signal with a time constant higher than a time needed for forming said critical level of said noxious gases and for producing a control signal and feeding the control signal to the source to modify the output signal of the sensor when the time constant is exceeded so as to compensate for a gradual change in concentration exceeding the time delay; and
   a comparator receiving said control signal and operatively connected with said voltage divider and with said control means, said comparator processing said control signal and a reference signal corresponding to said critical high level, said comparator switching the air-recirculation valve from an exterior air-supply position to an interior air-recirculation position upon said control signal exceeding said reference signal during a time at least equal to said time constant.

2. The gas-sensing system defined in claim 1 wherein said source is a controlled current or voltage source, said controlling means being connected with said current or voltage source and forming a feedback loop realizing said time delay.

3. The gas-sensing system defined in claim 2 wherein said means for controlling include a resistor-capacitor combination.

4. The gas-sensing system defined in claim 1 wherein said controlling means is a microprocessor provided with an A/D converter and with a binary register, said output signal being digitized and said reference signal being sorted in said microprocessor.

5. The gas-sensing system defined in claim 4 wherein said reference signal is varied with respect to a level of the noxious gases prior to being stored.

6. The gas-sensing system defined in claim 4, further comprising means for heating said sensor, said means for heating including a filament and being connected with said means for controlling, said means for heating receiving another signal from said means for controlling, said other signal being in a form of pulses, a first pulse switching said means for heating and being conveyed for a time period longer than a time period of each of following pulses, said first pulse heating said sensor with a filament power about twice as much as each of said following pulses, said following pulses being identical.

7. The gas-sensing system defined in claim 1 wherein said time constant is varied from a few hours to a few minutes.

8. The gas-sensing system defined in claim 1 wherein said comparator is a switching transistor connected with said controlling means.

* * * * *